United States Patent
Chen et al.

(10) Patent No.: US 10,920,201 B2
(45) Date of Patent: Feb. 16, 2021

(54) RICE EPSPS MUTANT, ENCODING GENE AND USE THEREOF

(71) Applicant: GEVOTO LLC, Chengdu (CN)

(72) Inventors: Rong Chen, Chengdu (CN); Longqun Deng, Chengdu (CN); Yuangen Lu, Chengdu (CN); Ling Li, Chengdu (CN); Xiaorong Feng, Chengdu (CN); Nanfei Xu, Chengdu (CN)

(73) Assignee: GEVOTO LLC, Chengdu (CN)

( * ) Notice: Subject to any disclaimer, the term of this patent is extended or adjusted under 35 U.S.C. 154(b) by 0 days.

(21) Appl. No.: 16/474,519

(22) PCT Filed: Jun. 30, 2017

(86) PCT No.: PCT/CN2017/091001
§ 371 (c)(1),
(2) Date: Jun. 27, 2019

(87) PCT Pub. No.: WO2018/120707
PCT Pub. Date: Jul. 5, 2018

(65) Prior Publication Data
US 2019/0345464 A1   Nov. 14, 2019

(30) Foreign Application Priority Data

Dec. 28, 2016   (CN) .......................... 201611242510.5

(51) Int. Cl.
*C12N 9/10*         (2006.01)
*C12N 15/82*        (2006.01)

(52) U.S. Cl.
CPC ....... *C12N 9/1092* (2013.01); *C12N 15/8274* (2013.01); *C12Y 205/01019* (2013.01)

(58) Field of Classification Search
CPC . C12N 9/1092; C12N 15/827; C12N 15/8274
See application file for complete search history.

(56) References Cited

U.S. PATENT DOCUMENTS

| 10,655,141 B2 * | 5/2020 | Dong ................. C12N 15/8275 |
| 2003/0049814 A1 | 3/2003 | Andrews et al. |
| 2008/0227966 A1 | 9/2008 | Barry et al. |

FOREIGN PATENT DOCUMENTS

| CN | 1359422 A | 7/2002 |
| CN | 1810962 A | 8/2006 |
| CN | 101508996 A | 8/2009 |
| CN | 102994526 A | 3/2013 |
| CN | 104232600 A | 12/2014 |
| CN | 105969782 A | 9/2016 |
| CN | 106636025 A | 5/2017 |
| EP | 2465341 A1 | 6/2012 |
| WO | WO 03/013226 A2 | 2/2003 |
| WO | WO 2004/009761 A2 | 1/2004 |

OTHER PUBLICATIONS

Cao, Gaoyi, et al. "A novel 5-enolpyruvylshikimate-3-phosphate synthase shows high glyphosate tolerance in *Escherichia coli* and tobacco plants." PLoS One 7.6 (2012): e38718. (Year: 2012).*
International Search Report and Written Opinion corresponding to International Patent Application No. PCT/CN2017/091001 dated Sep. 21, 2017.
Notification to Grant Patent for Chinese Patent Application No. 201611242510.5 dated Oct. 11, 2017.
Office Action corresponding to Chinese Patent Application No. 201611242510.5 dated Aug. 17, 2017.
Search Report corresponding to Chinese Patent Application No. 201611242510.5 dated Aug. 14, 2017.
Supplementary Search Report corresponding to Chinese Patent Application No. 201611242510.5 dated Sep. 22, 2017.
Zhou et al., "Identification of a Glyphosate-Resistant Mutant of Rice 5-Enolpyruvylshikimate 3-Phosphate Synthase Using a Directed Evolution Strategy," Plant Physiology, vol. 140, pp. 184-195 (2006).
English Translation of the IPRP corresponding to International Patent Application No. PCT/CN2017/091001 dated Jul. 2, 2019.
English Translation of the Written Opinion corresponding to International Patent Application No. PCT/CN2017/091001 dated Sep. 21, 2017.

* cited by examiner

*Primary Examiner* — Lee A Visone
(74) *Attorney, Agent, or Firm* — Jenkins, Wilson, Taylor & Hunt, P.A.

(57) ABSTRACT

A paddy rice EPSPS mutant, and an encoding gene and use thereof, relating to the technical field of genetic engineering. The paddy rice EPSPS mutant has an amino acid sequence shown as SEQ ID NO. 1. The paddy rice EPSPS mutant has glyphosate resistance and can resist glyphosate having a concentration of 100 mM. The paddy rice EPSPS mutant has very wide use prospect in the field of cultivating glyphosate-resistant plants.

11 Claims, 3 Drawing Sheets
Specification includes a Sequence Listing.

```
OsE    ATGGCGTCCAACGCCGCGGCTGCGGCGGCGAAGGCGGAGG    40
       M  A  S  N  A  A  A  A  A  A  K  A  E
OsEM   ATGGCGTCCAACGCCGCGGCTGCGGCGGCGAAGGCGGAGG    40
       M  A  S  N  A  A  A  A  A  A  K  A  E

OsE    CCTGAAAGCCCTCGGGCTCTCTGTGGAAGCAGATAAAGTT    240
       L  K  A  L  G  L  S  V  E  A  D  K  V
OsEM   CCTGAAAGGCCTCGGGCTCTCTGTGGAAGCAGATAAAGTT    240
       L  K  G  L  G  L  S  V  E  A  D  K  V

OsE    GGGGAACGCTGGAACTGCAATGCGACCATTGACAGCAGCC    360
       G  N  A  G  T  A  M  R  P  L  T  A  A
OsEM   GGGGAACGCTGCGACTGCAATGCGATCCTTGACAGCAGCC    360
       G  N  A  A  T  A  M  R  S  L  T  A  A

OsE    TGTCGGGTTGAAACAACTTGGTGCGGATGTCGACTGTTTC    480
       V  G  L  K  Q  L  G  A  D  V  D  C  F
OsEM   TGTCGGGTTGAAACGACTTGGTGCGGATGTCGACTGTTTC    480
       V  G  L  K  R  L  G  A  D  V  D  C  F

OsE    TTGGCCCTTGGGGATGTGGAGATCGAAATCATTGACAAAC    640
       L  A  L  G  D  V  E  I  E  I  I  D  K
OsEM   TTGGCCCTTGGGGATGTGGAGATCGAAATCATTGACAGAC    640
       L  A  L  G  D  V  E  I  E  I  I  D  R

OsE    GACAGATTCTATATTAAGGGAGGGCAGAAGTACAAATCTC    760
       D  R  F  Y  I  K  G  G  Q  K  Y  K  S
OsEM   GACAGATTCTATATTAAGGGAGGGCAGCAGTACGAATCTC    760
       D  R  F  Y  I  K  G  G  Q  Q  Y  E  S

OsE    TCAACATGAACAAAATGCCTGATGTTGCCATGACCCTTGC    1040
       V  N  M  N  K  M  P  D  V  A  M  T  L  A
OsEM   TCAACATGAACAAAATGCCTGATGCTGCCATGACCCTTGC    1040
       V  N  M  N  K  M  P  D  A  A  M  T  L  A
```

RICE EPSPS MUTANT, ENCODING GENE AND USE THEREOF

The present disclosure claims the priority to the Chinese Patent Application No. CN201611242510.5, filed with the Chinese Patent Office on Dec. 28, 2016 and entitled "Rice EPSPS Mutant, Encoding Gene and Use thereof", the contents of which are incorporated in the present disclosure by reference in entirety.

TECHNICAL FIELD

The present disclosure relates to the technical field of genetic engineering, in particular to a rice EPSPS mutant, an encoding gene and use thereof.

BACKGROUND ART

Glyphosate is one of the most common herbicides currently used in the world, and has been used for nearly 40 years up to now. Glyphosate inhibits activity of 5-enolpyruvylshikimate-3-phosphate synthase (EPSPS). EPSPS catalyzes PEP and shikimate-3-phosphate to synthesize EPSP in a shikimic acid pathway, and finally leads to the synthesis of aromatic amino acid tryptophan, phenylalanine and tyrosine. Glyphosate blocks the synthesis of these aromatic amino acids, affecting normal growth of plants, and eventually causes death of affected plants.

At present, a method for creating a glyphosate-resistant crop is using genetic engineering to transform a glyphosate-resistant gene from bacteria into the plant (GMO), and then breed into commercial varieties. Since the launch in 1996, the planting acreage has increased quickly, and as of 2015, the cultivated area of the glyphosate-resistant GMO crops in the world has reached 150 million hectares, accounting for 83% of GMO acreage, bringing huge benefits to agricultural production and environment.

However, the most widely used glyphosate-resistant gene currently in agriculture is CP4 EPSPS derived from *Agrobacterium tumefaciens* CP4 strain. Although many EPSPS genes capable of resisting glyphosate have been found from microorganisms, these genes have not been widely used in crops. To use glyphosate-resistant genes from these microorganisms in crops, these genes, e.g. CP4 EPSPS, are expressed in crops through genetic formation, resulting in transgenic crops. Although genetically modified crops produced thereby have been commercialized at quite large scale, due to the anti-GMO (genetically modified organism) tide, acceptance level of the genetically modified crops is still quite low in the whole world, and even in America with the largest acreage of genetically modified crops, the genetically modified crops are limited to a few crops such as maize, soybean, and cotton.

SUMMARY

An objective of the present disclosure is to provide a rice EPSPS mutant (i.e. 5-enolpyruvylshikimate-3-phosphate synthase mutant), which is derived from rice, and has glyphosate resistance.

Another objective of the present disclosure is to provide an encoding gene, which encodes the above rice EPSPS mutant.

Another objective of the present disclosure is to provide a plasmid vector, which contains the above encoding gene.

Another objective of the present disclosure is to provide a recombinant bacterium or a recombinant cell containing the above plasmid vector.

Another objective of the present disclosure is to provide use of the above encoding gene in cultivating glyphosate-resistant plants.

Another objective of the present disclosure is to provide a primer for detecting the above encoding gene.

Another objective of the present disclosure is to provide a kit for detecting the above encoding gene.

Another objective of the present disclosure is to provide a method for improving resistance of plant to glyphosate.

The present disclosure is achieved as following:

A rice EPSPS mutant, which has an amino acid sequence represented by SEQ ID NO. 1.

An encoding gene, which encodes the above EPSPS mutant.

A plasmid vector, which contains the above encoding gene.

A recombinant bacterium or a recombinant cell containing the above plasmid vector.

Use of the above encoding gene in cultivating glyphosate-resistant plants.

A primer for detecting the above encoding gene.

A kit for detecting the above encoding gene, which includes the above primer.

A method for improving resistance of plant to glyphosate, which includes: expressing the above encoding gene in a target plant.

The Rice EPSPS Mutant, the Encoding Gene and the Use Thereof Provided in the Present Disclosure Include, for Example, Following Beneficial Effects:

Compared with an amino acid sequence (SEQ ID NO. 3) of wild-type rice EPSPS, the rice EPSPS mutant provided in the present disclosure, having an amino acid sequence represented by SEQ ID NO. 1, has multiple amino acid residue mutant sites, wherein, from terminal N to terminal C, an amino acid residue at position 70 is mutated from A to G, an amino acid residue at position 111 is mutated from G to A, an amino acid residue at position 116 is mutated from P to S, an amino acid residue at position 152 is mutated from Q to R, an amino acid residue at position 213 is mutated from K to R, an amino acid residue at position 250 is mutated from K to Q, an amino acid residue at position 252 is mutated from K to E, and an amino acid residue at position 342 is mutated from V to A, respectively. Mutation results of the above 8 sites enable the rice EPSPS mutant to have glyphosate resistance, and meanwhile maintain its own bio-enzyme catalytic activity, a plant or a recombinant bacterium transformed by the rice EPSPS mutant can grow normally, moreover, the rice EPSPS mutant, derived from rice, can be used to cultivate glyphosate-resistant plants such as rice, tobacco, soybean, maize, wheat, cotton and sorghum, and has a broad application prospect.

BRIEF DESCRIPTION OF DRAWINGS

In order to more clearly illustrate technical solutions of examples of the present disclosure, accompanying drawings used for description of the examples will be explained briefly below. It should be understood that the drawings below merely show some examples of the present disclosure, therefore, they should not be considered as limitation on the scope, and those ordinarily skilled in the art still could obtain other relevant drawings according to these accompanying drawings, without inventive effort.

DETAILED DESCRIPTION OF EMBODIMENTS

In order to make clearer of the objectives, technical solutions and features of the examples in the present disclosure, the technical solutions in the examples in the present disclosure will be described clearly and completely below. If no specific conditions are mentioned in the examples, they are carried out under normal conditions or conditions recommended by manufacturers. If the manufacturers of reagents or apparatus used are not specified, they are all conventional products commercially available.

A rice EPSPS mutant, and an encoding gene and use thereof in the examples of the present disclosure are specifically described below.

In one aspect, the present disclosure provides a rice EPSPS mutant (i.e. mutant of 5-enolpyruvylshikimate-3-phosphate synthase), which derives from rice, and has glyphosate resistance. The rice EPSPS mutant has an amino acid sequence as represented by SEQ ID NO. 1, consisting of 454 amino acid residues.

Figure 3:
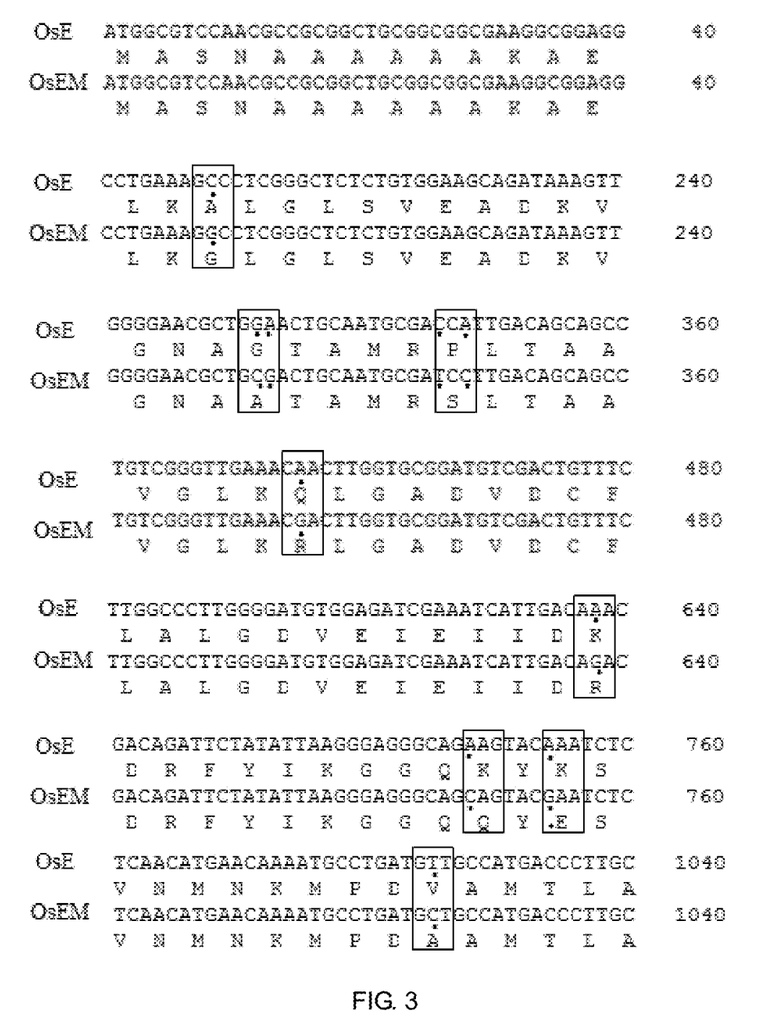
FIG. 3 shows a diagram of comparison results of part of sequences of OsEM gene (SEQ ID NO. 2) and OsE gene (SEQ ID NO. 3) provided in Example 1 of the present disclosure.

Compared with an amino acid sequence of a wild-type rice EPSPS (SEQ ID NO. 3), it has mutation at sites of multiple amino acid residues, wherein, from terminal N to terminal C, an amino acid residue at position 70 is mutated from A to G, an amino acid residue at position 111 is mutated from G to A, an amino acid residue at position 116 is mutated from P to S, an amino acid residue at position 152 is mutated from Q to R, an amino acid residue at position 213 is mutated from K to R, an amino acid residue at position 250 is mutated from K to Q, an amino acid residue at position 252 is mutated from K to E, and an amino acid residue at position 342 is mutated from V to A, respectively (as shown in FIG. 3), and a result of synergistic effect of the mutations at multiple sites enable the rice EPSPS mutant to be resistant to glyphosate, and meanwhile maintain its own biological activity.

In another aspect, the present disclosure provides an encoding gene, which encodes the above rice EPSPS mutant.

According to degeneracy of codon, an encoding sequence of the rice EPSPS mutant can be quite easily obtained on the basis of the amino acid sequence of the rice EPSPS mutant. The encoding sequence will fall within the scope of protection of the present disclosure as long as the above rice EPSPS mutant can be encoded.

Further, in some examples of the present disclosure, a base sequence of the encoding gene is represented by SEQ ID NO. 2.

Inventors of the present disclosure, using a rapid targeted evolution system, performed mismatch PCR on a wild-type EPSPS gene (SEQ ID NO. 4) derived from rice, and transformed a product into *E. coli* DH5a with EPSPS gene and C-P Lyase gene being knocked out, to obtain the encoding gene represented by SEQ ID NO. 2 after glyphosate resistance screening. This rapid targeted evolution system has a fast screening speed and high efficiency. Moreover, since double knockout *E. coli* was adopted as host bacterium, interference caused by endogenous gene mutation of the host bacterium is effectively eliminated, the mutant gene emerged from the screen is ensured to have corresponding glyphosate resistance, and false positive interference is effectively eliminated.

Compared with the wild-type EPSPS gene (SEQ ID NO. 4), from terminal 5' to terminal 3' of the encoding gene (SEQ ID NO. 2), a base at position 209 is mutated from C to G, two continuous bases at position 332 are mutated from GA to CG, a base at position 346 is mutated from C to T, a base at position 348 is mutated from A to C, a base at position 455 is mutated from A to G, a base at position 638 is mutated from A to G, a base at position 748 is mutated from A to C, a base at position 755 is mutated from A to G, and a base at position 1025 is mutated from T to C (as shown in FIG. 3). The mutation of the above bases directly causes mutation of amino acid residues at corresponding sites of the rice EPSPS mutant, endowing the rice EPSPS mutant with glyphosate resistance.

In another aspect, the present disclosure further provides a plasmid vector, which contains the above encoding gene.

Further, in some examples of the present disclosure, the plasmid vector is a plant expression vector.

Further, in some examples of the present disclosure, the above plant expression vector is a pB1121 vector.

In another aspect, the present disclosure further provides a recombinant bacterium or a recombinant cell containing the above plasmid vector.

In another aspect, the present disclosure further provides use of the above encoding gene in making and cultivating glyphosate-resistant plants.

Further, in some examples of the present disclosure, the use includes: linking the encoding gene to a plant expression vector, and transforming a target plant.

In the above, a method for transforming a target plant can be selected according to practical situations, for example, *Agrobacterium tumefaciens*-mediated method, particle bombardment and the like. It falls within the scope of protection of the present disclosure as long as the encoding gene provided in the present disclosure is utilized to cultivate glyphosate-resistant plants.

Besides, the type of the target plant can be selected according to practical requirements, which may be any one of rice, tobacco, soybean, maize, wheat, cotton and sorghum, and also may be other types of plants or crops, all of which fall within the scope of protection of the present disclosure.

Besides, it is easily understood that on the basis of the above encoding gene provided in the present disclosure, those skilled in the art could cultivate the glyphosate-resistant plants without the genetically modified technology, but take the encoding gene as a template, and modify an endogenous EPSPS gene of the target plant, for example, modify an encoding sequence of the endogenous EPSPS gene into a base sequence of the encoding gene, and encode in the target plant the same mutations as the rice EPSPS mutant provided in the present disclosure, such that the target plant has glyphosate resistance. Such use also falls within the scope of protection of the present disclosure.

In the above, the target plant includes, but is not limited to, rice, tobacco, soybean, maize, wheat, cotton and sorghum. Performing the above use in other types of plants also falls within the scope of protection of the present disclosure.

In another aspect, the present disclosure further provides a primer for detecting the above encoding gene. Further, in some examples of the present disclosure, the above primer includes a primer pair represented by SEQ ID NO. 5-6. In the above, the primer represented by SEQ ID NO. 5 is a forward primer, and the primer represented by SEQ ID NO. 6 is a reverse primer. The sequence of the encoding gene detected by the primer pair is represented by SEQ ID NO. 2.

It is easily understood that on the basis of the rice EPSPS mutant provided in the present disclosure, those skilled in the art could easily design a detection primer and an amplification primer according to the obtained gene sequence encoding the above rice EPSPS mutant, all of which fall within the scope of protection of the present disclosure.

In another aspect, the present disclosure further provides a method for improving resistance of plant to glyphosate, and the method includes: expressing the above encoding gene in a target plant.

Further, in some embodiments of the present disclosure, the above target plant is any one selected from a group consisting of rice, tobacco, soybean, maize, wheat, cotton and sorghum.

The features and performances of the present disclosure are further described below in detail in combination with examples.

Example 1

The present example provides a method for acquiring a rice EPSPS gene mutant and a rice EPSPS gene mutant obtained, including following specific steps.

1 Construction of a Mutant Pool of the Rice EPSPS Gene 1.1 mRNA of a wild-type rice EPSPS gene was reversely transcribed to cDNA (as represented by SEQ ID NO. 4) using a conventional method and cloned to a pADV5 vector.

1.2 A first round of mismatch PCR was performed using a forward primer PV325 and a reverse primer PV323, using a pADV5 vector containing the rice EPSPS gene as a template. The sequences of the primers used are as follows:

```
                                    (SEQ ID NO: 7)
PV325: 5'-TGAGCGCAACGCAATTAATGTGAG-3';
and
                                    (SEQ ID NO: 8)
PV323: 5'-CGTAAGGAGAAAATACCGCATCAGG-3'.
```

A PCR reaction system: 25.3 μL of $H_2O$, 4 μL of error-prone PCR MIX, 4 μL of error-prone PCR dNTP, 4 μL of $MnCl_2$, 0.8 μL of PV325 (10 μM), 0.8 μL of PV323 (10 μM), 0.1 μL of Taq polymerase, and 2 μL of the template.

A PCR reaction procedure: 95° C., 30 seconds; 60° C., 30 seconds; 72° C., 2 minutes; 40 cycles. A PCR product underwent 1% agarose electrophoresis, and then gel cutting and recovery to obtain a PCR product of the first round.

1.3 The above PCR product of the first round was taken as a template to perform a second round PCR using a forward primer 2M1H and a reverse primer 2M1T as shown below:

```
2M1H:
                                              (SEQ ID NO: 9)
5'-ttacgtacgttaattaATGGCGTCCAACGCCGCGGCTGCG-3'
2M1T:
                                             (SEQ ID NO: 10)
5'-ttacgtacgtcctgcaggTCAGTTCCTGACGAAAGTGCTTAGAACG-
3'.
```

A PCR reaction system: 31.9 μL of $H_2O$, 2.5 μL of DMSO, 5 μL of 10×PCR buffer, 5 μL of dNTP, 4 μL of $MgCl_2$, 0.5 μL of 2M1H (10 μM), 0.5 μL of 2M1T (10 μM), 0.1 μL of Taq polymerase, and 0.5 μL of the template (the PCR product of the first round).

A PCR reaction procedure: 95° C., 30 seconds; 60° C., 30 seconds; 72° C., 2 minutes; 60 cycles; 72° C., 10 min; maintained at 12° C.

1.4 1% agarose electrophoresis was performed on the PCR product obtained, and gel recovery and purification was performed for a gel strip at about 1.5 kb region consistent with that of a target strip.

1.5 The recovered product underwent Pac1 and Sbf1 double enzyme digestion, and then was linked using $T_4$ DNA ligase onto a new pADV5 vector that had undergone the same double enzyme digestion, to obtain a ligated product. The ligation product obtained in this step was a pADV5 vector carrying the rice EPSPS gene mutant, named as pADV5-EPSPS, which had a structure as shown in FIG. 1.

1.6 A double knockout *E. coli* was transformed (*E. Coli* DH5a with EPSPS gene and C-P Lyase gene being knocked out, named as EDCE, wherein for a preparation method thereof, reference can be made to a Chinese invention patent with the filing number CN2016103256926, entitled "Method for Screening Glyphosate-resistant Gene, EPSPS Mutant Gene, Defect Strain and Application Thereof").

The above ligation product (pADV5-EPSPS) was added to 50 μL of EDCE competent cells, fully mixed and disposed on ice for 30 min; underwent heat shock at 42° C. for 90 s, and ice bath for 2 min, and then 500 μL of LB liquid culture medium was added; the mixture underwent low-speed (150 r/min) shaking cultivation at 37° C. for 90 min.

After treatment in this step, the pADV5 vector carrying the rice EPSPS mutant gene was transformed into EDCE, and a transformed product, i.e. a rice EPSPS gene mutant pool, was obtained.

2 Resistance Screening 2.1 The above transformed product was centrifuged at a low speed, then inoculated into screening culture media (5 ml) containing glyphosate of different concentrations (glyphosate concentrations contained in the screening culture media were different from each other, and the concentrations of glyphosate contained therein were 10 mM, 20 mM, 50 mM, respectively, and of course, the glyphosate concentration could be set according to practical situations), and cultivated overnight at 37° C.

In the above, the screening culture media were culture media obtained by adding antibiotic, Spec (Spectinomycin), Gen (Gentamycin), Amp (Ampicillin) of certain concentrations and glyphosate of different concentrations, with M9 as a basic medium. Basic components of the M9 culture medium were as follows: $Na_2HPO_4$ 13~14 g/L, $KH_2PO_4$ 5.7~6.3 g/L, NaCl 0.9~1.1 g/L, NH$_4$Cl 1.8~2.2 g/L, glucose 37~43 g/L, MgSO$_4$·7H$_2$O 48~52 g/L, and CaCl$_2$) 21~23 g/L.

3 Sequencing and Sequence Alignment and Analysis 3.1 Monoclonal resistant bacteria growing on the screening culture media were separated, then samples were sent for sequencing, to detect the EPSPS gene sequence on pADV5-EPSPS, which had a base sequence represented by SEQ ID NO. 2, that is, the rice EPSPS mutant gene. The rice EPSPS mutant gene was named as OsEM gene. 5-enolpyruvylshikimate-3-phosphate synthase encoded thereby was named as a rice EPSPS mutant, having an amino acid sequence represented by SEQ ID NO. 1.

3.2 Sequences were aligned and analyzed, to compare and analyze the obtained OsEM gene and the wild-type rice EPSPS gene (SEQ ID NO. 4).

A result is as shown in FIG. 3: from terminal 5' to terminal 3' of the OsEM gene, a base at position 209 was mutated from C to G, two continuous bases at position 332 were mutated from GA to CG, a base at position 346 was mutated from C to T, a base at position 348 was mutated from A to C, a base at position 455 was mutated from A to G, a base at position 638 was mutated from A to G, a base at position 748 was mutated from A to C, a base at position 755 was mutated from A to G, and a base at position 1025 was mutated from T to C.

Figure 1:
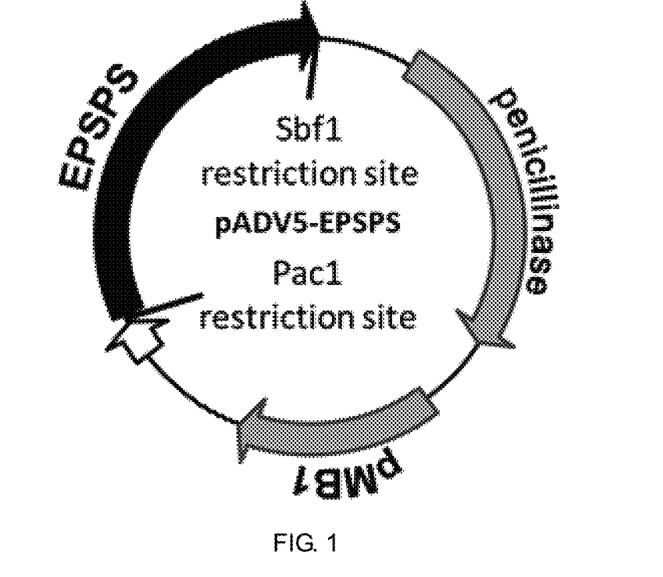
FIG. 1 is a schematic diagram of a pADV5-EPSPS vector provided in Example 1 of the present disclosure.
Figure 2:
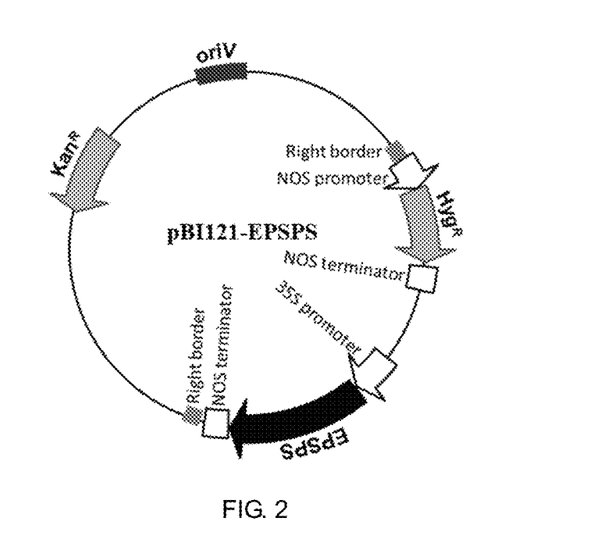
FIG. 2 is a schematic diagram of a pBI121-EPSPS vector provided in Example 3 of the present disclosure.

In the above, mutation of the base at position 209 from C to G caused an amino acid residue at position 70 of the rice EPSPS mutant to be mutated from A (alanine) to G (glycine);

mutation of the two continuous bases at position 332 from GA to CG caused an amino acid residue at position 111 of the rice EPSPS mutant to be mutated from G (glycine) to A (alanine);

mutation of the base at position 346 from C to T and mutation of the base at position 348 from A to C caused an amino acid residue at position 116 of the rice EPSPS mutant to be mutated from P (proline) to S (serine);

mutation of the base at position 455 from A to G caused an amino acid residue at position 152 of the rice EPSPS mutant to be mutated from Q (glutamine) to R (arginine);

mutation of the base at position 638 from A to G caused an amino acid residue at position 213 of the rice EPSPS mutant to be mutated from K (lysine) to R (arginine);

mutation of the base at position 748 from A to C caused an amino acid residue at position 250 of the rice EPSPS mutant to be mutated from K (lysine) to Q (glutamine);

mutation of the base at position 755 from A to G caused an amino acid residue at position 252 of the rice EPSPS mutant to be mutated from K (lysine) to E (glutamic acid); and mutation of the base at position 1025 from T to C caused an amino acid residue at position 342 of the rice EPSPS mutant to be mutated from V (valine) to A (alanine); there were 8 amino acid mutation sites in total (as shown by borders in FIG. 2).

Example 2

In the present example, EDCE transformed by the wild-type rice EPSPS gene (named as OsE gene, SEQ ID NO. 3) was taken as a control group, and the monoclonal resistant bacterium containing the OsEM gene (SEQ ID NO. 2) obtained in step 3.1 of Example 1 was taken as an experiment group, to detect the glyphosate resistance of the OsEM gene in bacteria.

The control group and the experiment group were respectively inoculated into culture media (screening culture media) containing glyphosate concentrations of 0 mM, 5 mM, 10 mM, 20 mM, 50 mM, 75 mM, and 100 mM, to observe growth states of bacterial colony in each group, denoted by growth saturation index (saturation index=0, no growth; saturation index=1, little growth; saturation index=2, half-saturated growth; saturation index=3, flourishing growth, but still having room to grow; saturation index=4, rapid growth, the bacteria having reached a highest (saturated) concentration in the culture media or the growth having reached the limit). Results are as shown in Table 1.

TABLE 1

Growth Saturation Index of Experiment Group Transformed by OsEM Gene and Control group Transformed by OsE Gene in Culture Media Containing Different Glyphosate Concentrations

| Group | Growth Saturation Index | | | | | | |
|---|---|---|---|---|---|---|---|
| | 0 mM | 5 mM | 10 mM | 20 mM | 50 mM | 75 mM | 100 mM |
| Control Group | 4 | 0 | 0 | 0 | 0 | 0 | 0 |
| Experiment Group | 4 | 4 | 4 | 4 | 4 | 4 | 4 |

The results in Table 1 show that in the culture medium containing 0 mM glyphosate, the experiment group (containing the OsEM gene) and the control group (containing the OsE gene) both could grow normally (the saturation index was 4 in both groups); but in the culture media containing 5 mM, 10 mM, 20 mM, 50 mM, 75 mM, 100 mM glyphosate, the control group could not grow (the saturation index was 0), while the experiment group could grow normally (the saturation index was 4). It thus indicates that the OsEM gene (SEQ ID NO. 2) obtained in Example 1 can endow EPSPS and C-P Lyase deficient *E. coli* with glyphosate resistance, such that it still maintains a growing state in the culture medium containing up to 100 mM glyphosate.

Besides, the glyphosate-resistant CP4-EPSPS gene mostly widely used currently in genetically modified crops in agriculture was further used in the present example as positive control, and *E. coli* respectively transformed by OsE gene (negative control group), OsEM gene (experiment group) and CP4-EPSPS gene (positive control group) were inoculated onto solid culture media respectively containing glyphosate of concentration of 0 mM, 1 mM, 50 mM, 100 mM, to observe growth states of bacterial colony in each group. Results are as shown in FIG. 4.

Figure 4:
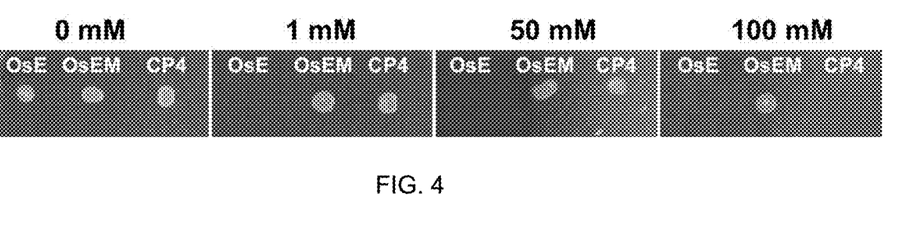
FIG. 4 shows growth of *E. coli* strain transformed with OsEM gene provided in Example 4 of the present disclosure, and wild-type OsE and CP4 positive control on media with different glyphosate concentrations.

Results in FIG. 4 show that on the culture medium containing 0 mM glyphosate, all of the experiment group (containing the OsEM gene) and the negative control group (containing the OsE gene) and the positive control group (containing the CP4 gene) could grow normally (there were obvious white plaques); but on the culture media containing 1 mM and 50 mM glyphosate, the negative control group (OsE) could not grow, while the experiment group (OsEM) and the positive control (CP4) could grow normally; and on the culture medium containing 100 mM glyphosate, neither the negative control group nor the positive control could grow, while the experiment group (OsEM) could grow normally. It thus indicates that the rice EPSPS mutant gene (OsEM gene, SEQ ID NO. 2) obtained in Example 1 can endow EPSPS and C-P Lyase deficient *E. coli* with glyphosate resistance, such that they still maintain a growing state in the culture medium containing up to 100 mM glyphosate, and their glyphosate resistance exceeds that of the CP4-EPSPS gene.

Example 3

The present example provides use of the above OsEM gene in making glyphosate-resistant tobacco. It includes following steps.

Preparation of a bacteria solution containing *Agrobacterium tumefaciens* 1.1 The plasmids (containing the OsEM gene) of the monoclonal resistant bacteria obtained in Example 1 were extracted in a conventional method, followed by PacI and SbfI double enzyme digestion, to isolate the small fragment, and then the small fragment was ligated, using T4 DNA ligase, to the pBI121 vectors that likewise had undergone double enzyme digestion, to obtain a pBI121-EPSPS vector having a structure as shown in FIG. 2.

1.2 GV3101 (*Agrobactrium tumefaciens*) competent cells were transformed with the pBI121-EPSPS vector, and single colonies were picked up to perform bacterial colony PCR detection to identify positive strains; then the positive strains were inoculated into 1 mL of YEP culture medium containing 50 μg·mL$^{-1}$ kanamycin and 50 μg·mL$^{-1}$ rifampin to propagate, and then preserved at −80° C., or used for subsequent experiment.

2 Tobacco Transformation 2.1 10 μL of preserved *Agrobactrium tumefaciens* culture in the above was pipetted, inoculated into 1 ml of a YEP liquid culture medium containing 50 μg·mL$^{-1}$ rifampin and 50 μg·mL$^{-1}$ kanamycin to be cultured at 28° C. with 200 r/min to OD$_{600}$ of 0.6-0.8, then cultured at an larger scale to OD$_{600}$ of about 0.5. The bacterial culture was diluted with an MS liquid culture medium (MS$_1$ culture medium without agar) and added with 20 mg/L AS as an infection solution.

2.2 Tobacco seeds (wild-type "Wisconsin38") were planted on a sterile culture medium, and leaves of 25-30 days old seedlings were chosen as transformation explants.

2.3 Veins and leaf margin of the leaves were removed, the leaves were cut into squares of 0.4×0.4 cm$^2$, soaked in the infection solution for 5-10 min, during which time the infection solution was continuously shaken such that it was in sufficient contact with the leaves.

2.6 The leaves were taken out with tweezers and put on sterile filter paper, after the bacterial solution was sucked out, the leaves were transferred into an MS$_1$ co-culture medium, and cultivated in the dark at 28° C. for 48 h.

2.7 The leaves were transferred onto an MS$_2$ induction and differentiation culture medium for selective culture. The leaves were transferred once every 15-20 days, and green shoots came up after 3-4 weeks. When the shoots grew to 1-2 cm high, adventitious buds were cut off, and the shoots were transferred into an MS$_3$ rooting medium to grow roots.

After strong roots were induced, the seedlings were taken out to wash the culture medium off the roots. The seedlings were transplanted to soil, and the survived plants were putatively transformed with OsEM gene, then the plants were transplanted to field or greenhouse or used for subsequent analysis.

3 Detection of Genetically Modified Plants

The tobacco plants transformed with OsEM gene were detected using the PCR method, and forward and reverse primers were designed according to the sequence of the OsEM gene and a tobacco reference gene (NtA). The primer sequences are as follows:

for the OsEM gene:
OSES53:
(SEQ ID NO. 5)
5'-GCAAGTTGTCCACCACTGTTGTGCC-3';

ATC5:
(SEQ ID NO. 6)
5'-CTGCAATGGTGTGCAGAACCCATC-3'; an
amplified fragment had a size of 300 bp;
and for the NtA reference gene:
NtAct5:
(SEQ ID NO: 11)
5'-CAGGTATTGTGTTGGATTCCGGCG-3';

NtAct3:
(SEQ ID NO: 12)
5'-CACTGTACTTGCGTTCAGGAGGCG-3'; an amplified
fragment had a size of 571 bp.

Genomic DNA of the tobacco plants transformed with OsEM gene obtained in step 2.7 in the present example were extracted respectively, and concentrations were adjusted to 100 ng/μL. They were used as genomic DNA templates.

A PCR detection system: 10 μL of 2×TsINGKe (Beijing TsingKe Biological Technology Co., Ltd), 2 μL of a primer mixture (10 μmol/L of OSES53, ATC5, NtAct5, NtAct3, 0.5 μL for each), 1 μL of the genomic DNA template (100 ng/μL), 7 μL ddH$_2$O.

A PCR detection procedure: 94° C., 3 min; 94° C., 30 s; 62° C., 30 s; 72° C., 45 s; 30 cycles; 72° C., 10 min; maintained at 12° C.

PCR amplification products underwent 1.5% agarose gel electrophoresis, wherein products having bands at position 300 bp and position 571 bp were positive tobacco plants transformed with OsEM gene.

Example 4

The present example provides use of the above OsEM gene in making glyphosate-resistant soybean, including following steps.

1 Transformation of Soybean with OsEM Gene 1.1 Seed disinfection and germination: soybean seeds (wild-type William 82) were sterilized dry with chlorine. Clean and plump seeds were chosen, placed, at 100 per plate, in a dryer, and disinfected with 100 ml of bleaching liquid added with 8 ml hydrochloric acid (12N) for 20 hours. The sterilized soybean seeds were then taken out, placed in a germination culture medium (sucrose 20 g/L+GELLAN GUM POWDER), and cultured in the dark at 25° C. for 2 days.

1.2 Infection and co-culture: when the *Agrobacterium* culture in step 1 of Example 3 reached OD$_{600}$ of 0.5-1.0, the culture was poured into a 50 ml centrifugal tube, and centrifuged (5000 rpm, 10 min). Supernatant was removed, an infection solution (B5, a large amount, trace amount and organic+sucrose 30 g/L+MES 3.9 g/L+GA3 0.25 mg/L+6-BA 1.67 mg/L+L-Cys 400 mg/L+AS 30 mg/L) was added to re-suspend the bacterium cells to OD$_{600}$ of 0.5-1.0, to be used as *Agrobacterium* mix for subsequent infection. Imbibed soybean seeds were transferred from the germination culture medium to a sterile Petri dish, and the seeds were cut longitudinally with a scalpel along a hilum, to separate cotyledon and hypo-cotyledon axis uniformly into two parts, after removing the seed coat, the material was used as explants in subsequent experiments.

1.3 The *Agrobacterium tumefaciens* resuspension mix was poured into a clean sterile culture dish, and about 200 explants were placed into the sterile culture dish to be infected at a room temperature for 1 hour. The explants were taken out, with scutella facing downward, placed on 5 ml of a co-culture medium (B5, large amount, trace amount and organic+sucrose 30 g/L+MES 3.9 g/L+GA3 0.25 mg/L+6-BA 1.67 mg/L+L-Cys 400 mg/L+DTT 154.2 mg/L+AS 30 mg/L) (the number of explants inoculated on the co-culture medium could be adjusted in different experiments), and the explants were co-cultured at 25° C. for 5 days.

1.4 Screening and regeneration: the co-cultured explants were transferred to a shoot-inducing culture medium (B5, large amount, trace amount and organic+sucrose 30 g/L+MES 0.59 g/L+GELLAN GUM POWDER+6-BA 1.67 mg/L+cefotaxime 400 mg/L+Glyphosate 15 mg/L), and cultured at 25° C. with a photoperiod of 16/8 h for 3 weeks.

1.5 When new shoots emerged, they were transferred to a shoot growth culture medium (B5, large amount, trace amount and organic+sucrose 30 g/L+MES 0.59 g/L+GELLAN GUM POWDER+6-BA 1.67 mg/L+cefotaxime 400 mg/L+Glyphosate 15 mg/L), and cultured in light at 25° C. with a photoperiod of 16/8 h for 3-5 weeks.

1.6 Buds 3-4 cm long were cut, transferred to a rooting medium (½ MS, large amount, trace amount, molysite, vitamin+sucrose 20 g/L+MES 0.59 g/L+GELLAN GUM POWDER+IAA 0.2/L) to be cultured in light at 25° C. with a photoperiod of 16/8 h until roots developed; after strong roots emerged, seedlings were taken out to wash off the culture medium on the root, and the seedlings were transplanted to soil, and the survived plants were putatively transformed with OsEM gene, then the plants were transplanted to field or greenhouse or used for subsequent analysis.

2 Detection of Genetically Modified Plants

The soybean plants transformed with OsEM gene were detected using the PCR method, a detection primer of the OsEM gene was the same as that in Example 3 (OSES53 and ATC5), and forward and reverse primers of the soybean reference gene (G C) had following sequences:

```
for the GmC reference gene:
                                    (SEQ ID NO: 13)
GmCons6F: 5'-CATGCTTTGGCTGTTGGAGATTTG-3';
and (SEQ ID NO: 14)
GmCons6R: 5'-GAACCTGATGGTGTTGGTAGAGGCG -3'; a
fragment had a size of 658 bp.
```

Genomic DNA of the transgenic soybean plants obtained in the above step 1.6 was extracted respectively (numbered respectively), adjusted to concentration of 100 ng/μL, and used as PCR templates.

A PCR detection system: 10 μL 2×TsINGKe, 2 μL of a primer mixture (10 μmol/L of OSES53, ATC5, GmCons6F, GmCons6R, 2 μL for each), 1 μL of genomic DNA template (100 ng/μL), 7 μL of ddH$_2$O.

A PCR detection procedure: 94° C., 3 min; 94° C., 30 s; 62° C., 30 s; 72° C., 45 s; 30 cycles; 72° C., 10 min; maintained at 12° C.

Figure 5:
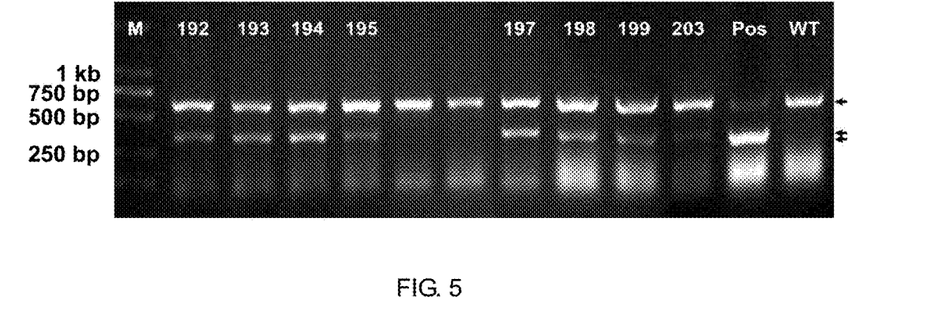
FIG. 5 shows results of gel electrophoresis of PCR detection of soybean plants transformed with OsEM gene provided in Example 4 of the present disclosure.

PCR amplification products underwent 1.5% agarose gel electrophoresis, wherein results are as shown in FIG. 5, and the products having bands at position 300 bp and position 658 bp were positive soybean plants transformed with OsEM gene.

The results in FIG. 5 show (in the figure: M is Marker, Pos is a positive control, WT is a wild-type plant, 192, 193, 194, 195, 197, 198, 199 and 203 are serial numbers of different soybean plants transformed with OsEM gene), and the soybean plants transformed with OsEM gene with the serial numbers 192, 193, 194, 195, 197, 198, 199 and 203 have two bands, which are taken as positive plants that were transformed with OsEM gene.

Example 5

In the present example, wild-type soybean plants were taken as controls, the positive soybean plants transformed with OsEM gene obtained in Example 4 were taken as experiment group, to verify glyphosate resistance of OsEM gene in plants. An experiment method is as follows:

1 The OsEM transformed positive soybean plants 10-20 cm tall and 3 wild-type soybean plants with a similar size were numbered and then randomly arranged in an experiment area (preventing leaves from overlapping).

2 The area with the plants was measured, and glyphosate was sprayed at a dosage of 1060 g/hectare (0.106 g/m$^2$).

3 Commercially available Roundup® 41% ammonium glyphosate was used. Amount was calculated according to the experiment area and dosage of 0.106 g/m$^2$, then diluted 20 times with water, and uniformly sprayed on the plants in the experiment area.

4 After leaf surfaces were dry, the plants in the experiment group and the control group were moved into a greenhouse.

5 Growth states of the plants were evaluated and recorded.

Statistical standards used to evaluate plant response to glyphosate were as follows: if a plant was not damaged by glyphosate at all and grew normally, it was considered as a plant with high glyphosate resistance, denoted by "+++"; if a plant showed leaves yellowed to some extent and grew slightly slow, it was considered as a plant with medium glyphosate resistance, denoted by "++"; if a plant had some leaves withered and grew quite slow, it was considered as a plant with low glyphosate resistance, denoted by "+"; if a plant withered and died, it was considered as a plant with no glyphosate resistance (having no glyphosate resistance), denoted by "−".

Figure 6:
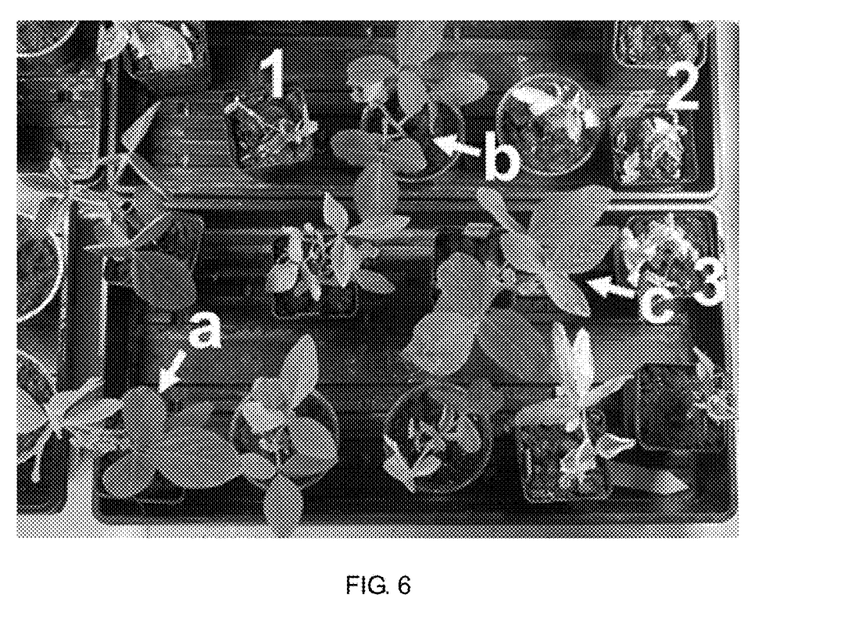
FIG. 6 shows a photograph of growth state of positive soybean plants transformed with OsEM gene provided in Example 5 of the present disclosure, on $7^{th}$ day after first spray of glyphosate.

After the glyphosate was sprayed, the growth states of the plants in each group were observed, captured and recorded on a 7$^{th}$ day, as shown in FIG. 6, and the number of plants with various types of resistance was counted. Results are shown in Table 2.

Figure 7:
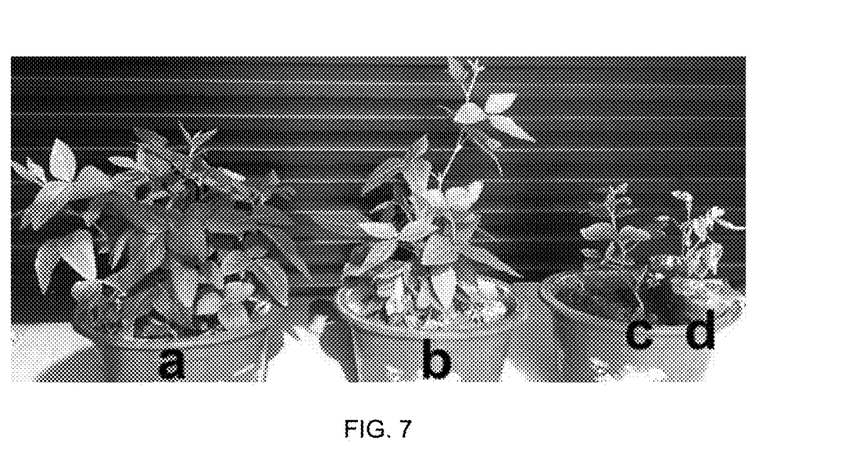
FIG. 7 shows a photograph of growth state of the positive soybean plants transformed with OsEM gene provided in Example 5 of the present disclosure on $14^{th}$ day after second spray of glyphosate.

Afterwards, plants grew well were transplanted to larger pots to grow, and the glyphosate (having a concentration of 1.06 g/m$^2$) was sprayed for a second time on a 21$^{st}$ day. After 2 weeks, the growth states of the plants in each group were captured and recorded. Results are as shown in FIG. 7.

TABLE 2

Statistic Results of Growth States of the Experiment Group and the Control Group in the Present Example on a 7$^{th}$ Day after Being Treated with Glyphosate for a First Time

| Group | Growth State | | | |
|---|---|---|---|---|
| | +++ | ++ | + | − |
| Control Group | 0 | 0 | 0 | 3 |
| Experiment Group | 4 | 1 | 3 | 2 |

Notes:
Numbers in the Table represent the number of plants

The Results in FIG. 6 (in the figure, 1, 2, and 3 are wild-type plants, and a, b, and c are transgenic plants) and Table 2 show that in the control group, none of 3 wild-type soybean plants showed glyphosate resistance, but in the experiment group, most of the positive soybean plants transformed with OsEM gene showed glyphosate resistance, wherein 4 plants showed high glyphosate resistance (as shown by a, b, and c in FIG. 6), 1 plant showed mediate glyphosate resistance, and 3 plants showed low glyphosate resistance.

Results in FIG. 7 show (in the figure, a, b and c are positive soybean plants transformed with OsEM gene, and d is a wild-type soybean plant) that the positive soybean plants with OsEM gene in the experiment group, after being treated with 1.06 g/m² glyphosate, could grow continuously, and showed a state of vigorous growth, dark-green leaves, tall plant and so on (as shown by a and b in FIG. 7); the positive soybean plants transformed with OsEM gene not having strong resistance (as shown by c in FIG. 7) grew slowly and had yellowing leaves; the wild-type soybean plants in the control group withered and died (as shown by d in FIG. 7).

The above results show that the OsEM gene not only can endow *E. coli* with the resistance to a concentration of 100 mM glyphosate, but also can endow the soybean plants with the resistance to a concentration of 1.06 g/m² glyphosate. The resistance of the OsEM gene is markedly higher than that of existing glyphosate-resistant genes, which exhibits superior glyphosate resistance, meanwhile, both the *E. coli* and the soybean plants transformed by the OsEM gene can grow normally, indicating that the bio-enzyme activity of the rice EPSPS mutant encoded by the OsEM gene is normal.

Example 6

The present example provides a primer pair for detecting the OsEM gene provided in Example 1, which includes a forward primer 5'-GCAAGTTGTCCAC-CACTGTTGTGCC-3' (SEQ ID NO. 5) and a reverse primer 5'-CTGCAATGGTGTGCAGAACCCATC-3' (SEQ ID NO. 6).

A method for detecting whether a sample to be tested contains components of the OsEM gene using the primer pair provided in the present example is as follows:
preparation of a PCR detection system: 10 μL of 2×TsINGKe, 0.5 μL of the forward primer (10 μmol/L), 0.5 μL of the reverse primer (10 μmol/L), 1 μL of DNA template (100 ng/μL), and 7 μL of ddH₂O; and
a PCR detection procedure: 94° C., 3 min; 94° C., 30 s; 62° C., 30 s; 72° C., 45 s; 30 cycles; 72° C., 10 min; maintained at 12° C.

PCR amplification products underwent 1.5% agarose gel electrophoresis, and the products having strips at position 300 bp contained the components of the OsEM gene.

Example 7

The present example provides a kit for detecting the OsEM gene provided in Example 1, wherein the kit includes the primer pair provided in Example 6. A method for detecting whether a sample to be tested contains components of the OsEM gene using the kit provided in the present example is substantially the same as that in Example 6.

To sum up, compared with the wild-type rice EPSPS (SEQ ID NO. 3) and the encoding gene thereof (SEQ ID NO. 4), the rice EPSPS mutant (SEQ ID NO. 1) and the encoding gene thereof (SEQ ID NO. 2) provided in the present disclosure have higher glyphosate resistance and all bio-enzyme activity; besides, the encoding gene (SEQ ID NO. 2), derived from the rice species per se rather than microorganisms, is applicable to transform various types of plants, for example, rice, tobacco, soybean, maize, cotton, sorghum, and wheat, and has a broader application range. Meanwhile, according to the sequence of the rice EPSPS mutant gene provided in the present disclosure, it can be used for cultivating new rice species having glyphosate resistance (non-transgenic method), to obtain conventional glyphosate-resistant non-transgenic species, and improve the degree of public acceptance to new varieties.

The above-mentioned are merely preferred examples of the present disclosure and are not used to limit the present disclosure. For those skilled in the art, various modifications and changes may be made to the present disclosure. Any amendments, equivalent replacements, improvements, and so on, within the spirit and principle of the present disclosure, should be covered by the scope of protection of the present disclosure.

INDUSTRIAL APPLICABILITY

Compared with the amino acid sequence (SEQ ID NO. 3) of the wild-type rice EPSPS, the rice EPSPS mutant provided in the present disclosure, having the amino acid sequence represented by SEQ ID NO. 1, has multiple amino acid residue mutant sites, wherein, from terminal N to terminal C, the amino acid residue at position 70 is mutated from A to G, the amino acid residue at position 111 is mutated from G to A, the amino acid residue at position 116 is mutated from P to S, the amino acid residue at position 152 is mutated from Q to R, the amino acid residue at position 213 is mutated from K to R, the amino acid residue at position 250 is mutated from K to Q, the amino acid residue at position 252 is mutated from K to E, and the amino acid residue at position 342 is mutated from V to A, respectively. Mutation results of the above 8 sites enable the rice EPSPS mutant to have glyphosate resistance, and meanwhile maintain its own bio-enzyme catalytic activity, the plant or the recombinant bacterium transformed by the encoding gene (for example, SEQ ID NO. 2) of the rice EPSPS mutant can grow normally, moreover, the rice EPSPS mutant, derived from rice, can be applied to cultivate glyphosate-resistant plants such as rice, tobacco, soybean, maize, wheat, cotton and sorghum.

What is claimed is:

1. A rice 5-enolpyruvylshikimate-3-phosphate synthase (EPSPS) mutant, wherein said rice EPSPS mutant comprises the amino acid sequence of SEQ ID NO. 1.

2. An encoding gene, wherein the encoding gene encodes the rice EPSPS mutant according to claim 1.

3. The encoding gene according to claim 2, wherein said encoding gene comprises SEQ ID NO. 2.

4. A method for cultivating glyphosate-resistant plants, wherein the method comprises: linking the encoding gene according to claim 2 to a plant expression vector, and transforming a target plant; or the method comprises: taking the encoding gene according to claim 2 as a template, and modifying an endogenous EPSPS gene of the target plant.

5. The method according to claim 4, wherein said encoding gene comprises SEQ ID NO. 2.

6. The method according to claim 4, wherein the target plant is any one selected from the group consisting of rice, tobacco, soybean, maize, wheat, cotton and sorghum.

7. The method according to claim 5, wherein the target plant is any one selected from the group consisting of rice, tobacco, soybean, maize, wheat, cotton and sorghum.

8. The method according to claim 4, wherein the plant expression vector is a pBI121 vector.

9. The method according to claim 5, wherein the plant expression vector is a pBI121 vector.

10. The method according to claim 6, wherein the plant expression vector is a pBI121 vector.

11. The method according to claim 7, wherein the plant expression vector is a pBI121 vector.

* * * * *

SEQUENCE LISTING

<160> NUMBER OF SEQ ID NOS: 14

<210> SEQ ID NO 1
<211> LENGTH: 454
<212> TYPE: PRT
<213> ORGANISM: Artificial sequence
<220> FEATURE:
<223> OTHER INFORMATION: Artificially synthesized polypeptide

<400> SEQUENCE: 1

```
Met Ala Ser Asn Ala Ala Ala Ala Lys Ala Glu Glu Ile Val
1               5                   10                  15

Leu Gln Pro Ile Arg Glu Ile Ser Gly Ala Val Gln Leu Pro Gly Ser
                20                  25                  30

Lys Ser Leu Ser Asn Arg Ile Leu Leu Leu Ser Ala Leu Ser Glu Gly
            35                  40                  45

Thr Thr Val Val Asp Asn Leu Leu Asn Ser Glu Asp Val His Tyr Met
    50                  55                  60

Leu Glu Ala Leu Lys Gly Leu Gly Leu Ser Val Glu Ala Asp Lys Val
65                  70                  75                  80

Ala Lys Arg Ala Val Val Gly Cys Gly Lys Phe Pro Val Glu
                85                  90                  95

Lys Asp Ala Lys Glu Glu Val Gln Leu Phe Leu Gly Asn Ala Ala Thr
                100                 105                 110

Ala Met Arg Ser Leu Thr Ala Ala Val Thr Ala Ala Gly Gly Asn Ala
            115                 120                 125

Thr Tyr Val Leu Asp Gly Val Pro Arg Met Arg Glu Arg Pro Ile Gly
        130                 135                 140

Asp Leu Val Val Gly Leu Lys Arg Leu Gly Ala Asp Val Asp Cys Phe
145                 150                 155                 160

Leu Gly Thr Glu Cys Pro Pro Val Arg Val Lys Gly Ile Gly Gly Leu
                165                 170                 175

Pro Gly Gly Lys Val Lys Leu Ser Gly Ser Ile Ser Ser Gln Tyr Leu
                180                 185                 190

Ser Ala Leu Leu Met Ala Ala Pro Leu Ala Leu Gly Asp Val Glu Ile
            195                 200                 205

Glu Ile Ile Asp Arg Leu Ile Ser Ile Pro Tyr Val Glu Met Thr Leu
210                 215                 220

Arg Leu Met Glu Arg Phe Gly Val Lys Ala Glu His Ser Asp Ser Trp
225                 230                 235                 240

Asp Arg Phe Tyr Ile Lys Gly Gln Gln Tyr Glu Ser Pro Gly Asn
            245                 250                 255

Ala Tyr Val Glu Gly Asp Ala Ser Ser Ala Ser Tyr Phe Leu Ala Gly
            260                 265                 270

Ala Ala Ile Thr Gly Gly Thr Val Thr Val Gln Gly Cys Gly Thr Thr
            275                 280                 285

Ser Leu Gln Gly Asp Val Lys Phe Ala Glu Val Leu Glu Met Met Gly
    290                 295                 300

Ala Lys Val Thr Trp Thr Asp Thr Ser Val Thr Val Thr Gly Pro Pro
305                 310                 315                 320

Arg Glu Pro Tyr Gly Lys Lys His Leu Lys Ala Val Asp Val Asn Met
                325                 330                 335

Asn Lys Met Pro Asp Ala Ala Met Thr Leu Ala Val Val Ala Leu Phe
            340                 345                 350

Ala Asp Gly Pro Thr Ala Ile Arg Asp Val Ala Ser Trp Arg Val Lys
        355                 360                 365

Glu Thr Glu Arg Met Val Ala Ile Arg Thr Glu Leu Thr Lys Leu Gly
    370                 375                 380

Ala Ser Val Glu Glu Gly Pro Asp Tyr Cys Ile Ile Thr Pro Pro Glu
385                 390                 395                 400

Lys Leu Asn Ile Thr Ala Ile Asp Thr Tyr Asp Asp His Arg Met Ala
                405                 410                 415
```

```
Met Ala Phe Ser Leu Ala Ala Cys Ala Asp Val Pro Val Thr Ile Arg
            420                 425                 430

Asp Pro Gly Cys Thr Arg Lys Thr Phe Pro Asn Tyr Phe Asp Val Leu
        435                 440                 445

Ser Thr Phe Val Arg Asn
    450
```

<210> SEQ ID NO 2
<211> LENGTH: 1365
<212> TYPE: DNA
<213> ORGANISM: Artificial sequence
<220> FEATURE:
<223> OTHER INFORMATION: Artificially synthesized nucleic acid sequence

<400> SEQUENCE: 2

```
atggcgtcca acgccgcggc tgcggcggcg aaggcggagg agatcgtgct ccagcccatc      60
agggagatct ccggggcggt tcagctgcca gggtccaagt cgctctccaa caggatcctc    120
ctcctctccg ccctctccga ggcacaaca gtggtggaca acttgctgaa cagtgaggat    180
gttcactaca tgcttgaggc cctgaaaggc ctcgggctct ctgtggaagc agataaagtt    240
gcaaaaagag ctgtagtcgt tggctgtggt ggcaagtttc ctgttgagaa ggatgcgaaa    300
gaggaagtgc aactcttctt ggggaacgct gcgactgcaa tgcgatcctt gacagcagcc    360
gtgactgctg ctggtggaaa tgcaacttat gtgcttgatg gagtgccacg aatgagggag    420
agaccgattg gtgacttggt tgtcgggttg aaacgacttg gtgcggatgt cgactgtttc    480
cttggcactg aatgcccacc tgttcgtgtc aagggaattg gaggacttcc tggtggcaag    540
gttaagctct ctggttccat cagcagtcag tacttgagtg ccttgctgat ggctgctcct    600
ttggcccttg gggatgtgga gatcgaaatc attgacagac taatctccat tccttacgtt    660
gaaatgacat tgagattgat ggagcgtttt ggtgtgaagg cagagcattc tgatagttgg    720
gacagattct atattaaggg agggcagcag tacgaatctc ctggaaatgc ctatgttgaa    780
ggtgatgcct caagcgcgag ctatttcttg gctggtgctg caatcactgg aggcactgtg    840
acagttcaag ttgtggtac gaccagtttg caggtgatg tcaaatttgc tgaggtactt    900
gagatgatgg gagcaaaggt tacatggact gacaccagt taaccgtaac tggtccacca    960
cgtgagcctt atgggaagaa acacctgaaa gctgttgatg tcaacatgaa caaaatgcct   1020
gatgctgcca tgacccttgc cgttgttgca ctcttcgctg atggtccaac tgctatcaga   1080
gatgtggctt cctggagagt aaaggaaacc gaaaggatgg ttgcaattcg gaccgagcta   1140
acaaagctgg gagcatcggt tgaagaaggt cctgactact gcatcatcac cccaccggag   1200
aagctgaaca tcacggcaat cgacacctac gatgatcaca ggatggccat ggccttctcc   1260
ctcgctgcct cgccgacgt gcccgtgacg atcagggacc ctggttgcac ccgcaagacc   1320
ttccccaact acttcgacgt tctaagcact ttcgtcagga actga                    1365
```

<210> SEQ ID NO 3
<211> LENGTH: 454
<212> TYPE: PRT
<213> ORGANISM: Oryza sativa

<400> SEQUENCE: 3

```
Met Ala Ser Asn Ala Ala Ala Ala Ala Lys Ala Glu Glu Ile Val
1               5                   10                  15

Leu Gln Pro Ile Arg Glu Ile Ser Gly Ala Val Gln Leu Pro Gly Ser
            20                  25                  30
```

-continued

```
Lys Ser Leu Ser Asn Arg Ile Leu Leu Ser Ala Leu Ser Glu Gly
         35                  40                  45
Thr Thr Val Val Asp Asn Leu Leu Asn Ser Glu Asp Val His Tyr Met
 50                  55                  60
Leu Glu Ala Leu Lys Ala Leu Gly Leu Ser Val Glu Ala Asp Lys Val
 65                  70                  75                  80
Ala Lys Arg Ala Val Val Gly Cys Gly Lys Phe Pro Val Glu
                 85                  90                  95
Lys Asp Ala Lys Glu Glu Val Gln Leu Phe Leu Gly Asn Ala Ala Thr
                100                 105                 110
Ala Met Arg Leu Leu Thr Ala Ala Val Thr Ala Gly Gly Asn Ala
                115                 120                 125
Thr Tyr Val Leu Asp Gly Val Pro Arg Met Arg Glu Arg Pro Ile Gly
                130                 135                 140
Asp Leu Val Val Gly Leu Lys Gln Leu Gly Ala Asp Val Asp Cys Phe
145                 150                 155                 160
Leu Gly Thr Glu Cys Pro Pro Val Arg Val Lys Gly Ile Gly Gly Leu
                165                 170                 175
Pro Gly Gly Lys Val Lys Leu Ser Gly Ser Ile Ser Ser Gln Tyr Leu
                180                 185                 190
Ser Ala Leu Leu Met Ala Ala Pro Leu Ala Leu Gly Asp Val Glu Ile
                195                 200                 205
Glu Ile Ile Asp Lys Leu Ile Ser Ile Pro Tyr Val Glu Met Thr Leu
                210                 215                 220
Arg Leu Met Glu Arg Phe Gly Val Lys Ala Glu His Ser Asp Ser Trp
225                 230                 235                 240
Asp Arg Phe Tyr Ile Lys Gly Gly Gln Lys Tyr Glu Ser Pro Gly Asn
                245                 250                 255
Ala Tyr Val Glu Gly Asp Ala Ser Ser Ala Ser Tyr Phe Leu Ala Gly
                260                 265                 270
Ala Ala Ile Thr Gly Gly Thr Val Thr Val Gln Gly Cys Gly Thr Thr
                275                 280                 285
Ser Leu Gln Gly Asp Val Lys Phe Ala Glu Val Leu Glu Met Met Gly
                290                 295                 300
Ala Lys Val Thr Trp Thr Asp Thr Ser Val Thr Val Thr Gly Pro Pro
305                 310                 315                 320
Arg Glu Pro Tyr Gly Lys Lys His Leu Lys Ala Val Asp Val Asn Met
                325                 330                 335
Asn Lys Met Pro Asp Val Ala Met Thr Leu Ala Val Val Ala Leu Phe
                340                 345                 350
Ala Asp Gly Pro Thr Ala Ile Arg Asp Val Ala Ser Trp Arg Val Lys
                355                 360                 365
Glu Thr Glu Arg Met Val Ala Ile Arg Thr Glu Leu Thr Lys Leu Gly
                370                 375                 380
Ala Ser Val Glu Glu Gly Pro Asp Tyr Cys Ile Ile Thr Pro Pro Glu
385                 390                 395                 400
Lys Leu Asn Ile Thr Ala Ile Asp Thr Tyr Asp Asp His Arg Met Ala
                405                 410                 415
Met Ala Phe Ser Leu Ala Ala Cys Ala Asp Val Pro Val Thr Ile Arg
                420                 425                 430
Asp Pro Gly Cys Thr Arg Lys Thr Phe Pro Asn Tyr Phe Asp Val Leu
                435                 440                 445
Ser Thr Phe Val Arg Asn
```

<210> SEQ ID NO 4
<211> LENGTH: 1365
<212> TYPE: DNA
<213> ORGANISM: Oryza sativa

<400> SEQUENCE: 4

| | | | | | |
|---|---|---|---|---|---|
| atggcgtcca | acgccgcggc | tgcggcggcg | aaggcggagg | agatcgtgct | ccagcccatc | 60 |
| agggagatct | ccggggcggt | tcagctgcca | gggtccaagt | cgctctccaa | caggatcctc | 120 |
| ctcctctccg | ccctctccga | gggcacaaca | gtggtggaca | acttgctgaa | cagtgaggat | 180 |
| gttcactaca | tgcttgaggc | cctgaaagcc | ctcgggctct | ctgtggaagc | agataaagtt | 240 |
| gcaaaaagag | ctgtagtcgt | tggctgtggt | ggcaagtttc | ctgttgagaa | ggatgcgaaa | 300 |
| gaggaagtgc | aactcttctt | ggggaacgct | gcgactgcaa | tgcgactctt | gacagcagcc | 360 |
| gtgactgctg | ctggtggaaa | tgcaacttat | gtgcttgatg | gagtgccacg | aatgagggag | 420 |
| agaccgattg | gtgacttggt | tgtcgggttg | aaacaacttg | gtgcggatgt | cgactgtttc | 480 |
| cttggcactg | aatgcccacc | tgttcgtgtc | aagggaattg | gaggacttcc | tggtggcaag | 540 |
| gttaagctct | ctggttccat | cagcagtcag | tacttgagtg | ccttgctgat | ggctgctcct | 600 |
| ttggcccttg | gggatgtgga | gatcgaaatc | attgacaaac | taatctccat | tccttacgtt | 660 |
| gaaatgacat | tgagattgat | ggagcgtttt | ggtgtgaagg | cagagcattc | tgatagttgg | 720 |
| gacagattct | atattaaggg | agggcagaag | tacaaatctc | ctggaaatgc | ctatgttgaa | 780 |
| ggtgatgcct | caagcgcgag | ctatttcttg | gctggtgctg | caatcactgg | aggcactgtg | 840 |
| acagttcaag | gttgtggtac | gaccagtttg | cagggtgatg | tcaaatttgc | tgaggtactt | 900 |
| gagatgatgg | gagcaaaggt | tacatggact | gacaccagtg | taaccgtaac | tggtccacca | 960 |
| cgtgagcctt | atgggaagaa | acacctgaaa | gctgttgatg | tcaacatgaa | caaaatgcct | 1020 |
| gatgttgcca | tgacccttgc | cgttgttgca | ctcttcgctg | atggtccaac | tgctatcaga | 1080 |
| gatgtggctt | cctggagagt | aaaggaaacc | gaaaggatgg | ttgcaattcg | gaccgagcta | 1140 |
| acaaagctgg | gagcatcggt | tgaagaaggt | cctgactact | gcatcatcac | cccaccggag | 1200 |
| aagctgaaca | tcacggcaat | cgacacctac | gatgatcaca | ggatggccat | ggccttctcc | 1260 |
| ctcgctgcct | gcgccgacgt | gcccgtgacg | atcagggacc | ctggttgcac | ccgcaagacc | 1320 |
| ttccccaact | acttcgacgt | tctaagcact | ttcgtcagga | actga | | 1365 |

<210> SEQ ID NO 5
<211> LENGTH: 25
<212> TYPE: DNA
<213> ORGANISM: Artificial sequence
<220> FEATURE:
<223> OTHER INFORMATION: Artificially synthesized oligonucleotide
      sequence

<400> SEQUENCE: 5
gcaagttgtc caccactgtt gtgcc                                           25

<210> SEQ ID NO 6
<211> LENGTH: 24
<212> TYPE: DNA
<213> ORGANISM: Artificial sequence
<220> FEATURE:
<223> OTHER INFORMATION: Artificially synthesized oligonucleotide
      sequence

<400> SEQUENCE: 6
ctgcaatggt gtgcagaacc catc                                        24

<210> SEQ ID NO 7
<211> LENGTH: 24
<212> TYPE: DNA
<213> ORGANISM: Artificial sequence
<220> FEATURE:
<223> OTHER INFORMATION: Artificially synthesized oligonucleotide
      sequence

<400> SEQUENCE: 7
tgagcgcaac gcaattaatg tgag                                        24

<210> SEQ ID NO 8
<211> LENGTH: 25
<212> TYPE: DNA
<213> ORGANISM: Artificial Sequence
<220> FEATURE:
<223> OTHER INFORMATION: Artificially synthesized oligonucleotide
      sequence

<400> SEQUENCE: 8
cgtaaggaga aaataccgca tcagg                                       25

<210> SEQ ID NO 9
<211> LENGTH: 40
<212> TYPE: DNA
<213> ORGANISM: Artificial Sequence
<220> FEATURE:
<223> OTHER INFORMATION: Artificially synthesized oligonucleotide
      sequence

<400> SEQUENCE: 9
ttacgtacgt taattaatgg cgtccaacgc cgcggctgcg                       40

<210> SEQ ID NO 10
<211> LENGTH: 46
<212> TYPE: DNA
<213> ORGANISM: Artificial Sequence
<220> FEATURE:
<223> OTHER INFORMATION: Artificially synthesized oligonucleotide
      sequence

<400> SEQUENCE: 10
ttacgtacgt cctgcaggtc agttcctgac gaaagtgctt agaacg                46

<210> SEQ ID NO 11
<211> LENGTH: 24
<212> TYPE: DNA
<213> ORGANISM: Artificial Sequence
<220> FEATURE:
<223> OTHER INFORMATION: Artificially synthesized oligonucleotide
      sequence

<400> SEQUENCE: 11
caggtattgt gttggattcc ggcg                                        24

<210> SEQ ID NO 12
<211> LENGTH: 24
<212> TYPE: DNA
<213> ORGANISM: Artificial Sequence
<220> FEATURE:
<223> OTHER INFORMATION: Artificially synthesized oligonucleotide
      sequence

<400> SEQUENCE: 12

```
cactgtactt gcgttcagga ggcg                                              24

<210> SEQ ID NO 13
<211> LENGTH: 24
<212> TYPE: DNA
<213> ORGANISM: Artificial Sequence
<220> FEATURE:
<223> OTHER INFORMATION: Artificially synthesized oligonucleotide
      sequence

<400> SEQUENCE: 13
catgctttgg ctgttggaga tttg                                              24

<210> SEQ ID NO 14
<211> LENGTH: 25
<212> TYPE: DNA
<213> ORGANISM: Artificial Sequence
<220> FEATURE:
<223> OTHER INFORMATION: Artificially synthesized oligonucleotide
      sequence

<400> SEQUENCE: 14
gaacctgatg gtgttggtag aggcg                                             25
```